United States Patent [19]

Krull et al.

[11] Patent Number: 4,637,861
[45] Date of Patent: Jan. 20, 1987

[54] STABILIZED, LIPID MEMBRANE-BASED DEVICE AND METHOD OF ANALYSIS

[75] Inventors: Ulrich J. Krull, Weston; Michael Thompson, Mississauga, both of Canada

[73] Assignee: Allied Corporation, Morris Township, Morris County, N.J.

[21] Appl. No.: 809,691

[22] Filed: Dec. 16, 1985

[51] Int. Cl.$^4$ ................. G01N 27/30; G01N 27/40
[52] U.S. Cl. ...................... 204/1 T; 204/403;
204/418; 435/291; 435/817; 436/501; 436/806
[58] Field of Search ............ 204/403, 418, 1 T, 1 A, 204/1 K; 436/501, 806; 435/291, 817; 357/25

[56] References Cited

U.S. PATENT DOCUMENTS

| | | | |
|---|---|---|---|
| 3,607,700 | 9/1971 | Tosteson | 204/1 T X |
| 4,321,123 | 3/1982 | Nakamura et al. | 204/403 |
| 4,490,216 | 12/1984 | McConnell | 204/1 T |
| 4,562,157 | 12/1985 | Lowe et al. | 435/291 |

FOREIGN PATENT DOCUMENTS 488805  6/1975  Australia ............... 436/806

OTHER PUBLICATIONS

Bauer et al., *Desalination*, 46: 369 (1983).
Thompson and Krull, *Analytica Chimica Acta*, 147: 1-21 (1983).
Thompson et al., *Analytica Chimica Acta*, 117: 133-145 (1980).
Albrecht et al., *Biochimica et Biophysica Acta*, 687: 165-169 (1982).
Kuhn, *Thin Solid Films*, 99: 1-16 (1983).
Krull et al., Abstract 11-2, 67th Annual CIC Conference (Jun. 1984).
Heckmann et al., *Thin Solid Films*, 99: 265 (1983).

*Primary Examiner*—G. L. Kaplan
*Attorney, Agent, or Firm*—Jay P. Friedenson; Gerhard H. Fuchs

[57] ABSTRACT

A stabilized, lipid membrane-based device is provided. This device includes a plurality of membrane-forming lipids, and a support for stabilizing the lipid membrane. Each membrane-forming lipid includes a long chain through which the lipid is anchored to a binding site on the support, and another long chain unattached to the support. The support binding sites are spaced apart from one another to provide the lipid membrane with an appropriate molecular packing density.

Also provided is a process for determining the concentration of a selected chemical species in an aqueous electrolytic solution, using an electrochemical cell formed from a lipid membrane-based device in accordance with the present invention. This process includes the step of applying across the lipid membrane of the device an electrical potential difference to produce an analytical signal based upon an increase in membrane ion permeability.

15 Claims, 4 Drawing Figures

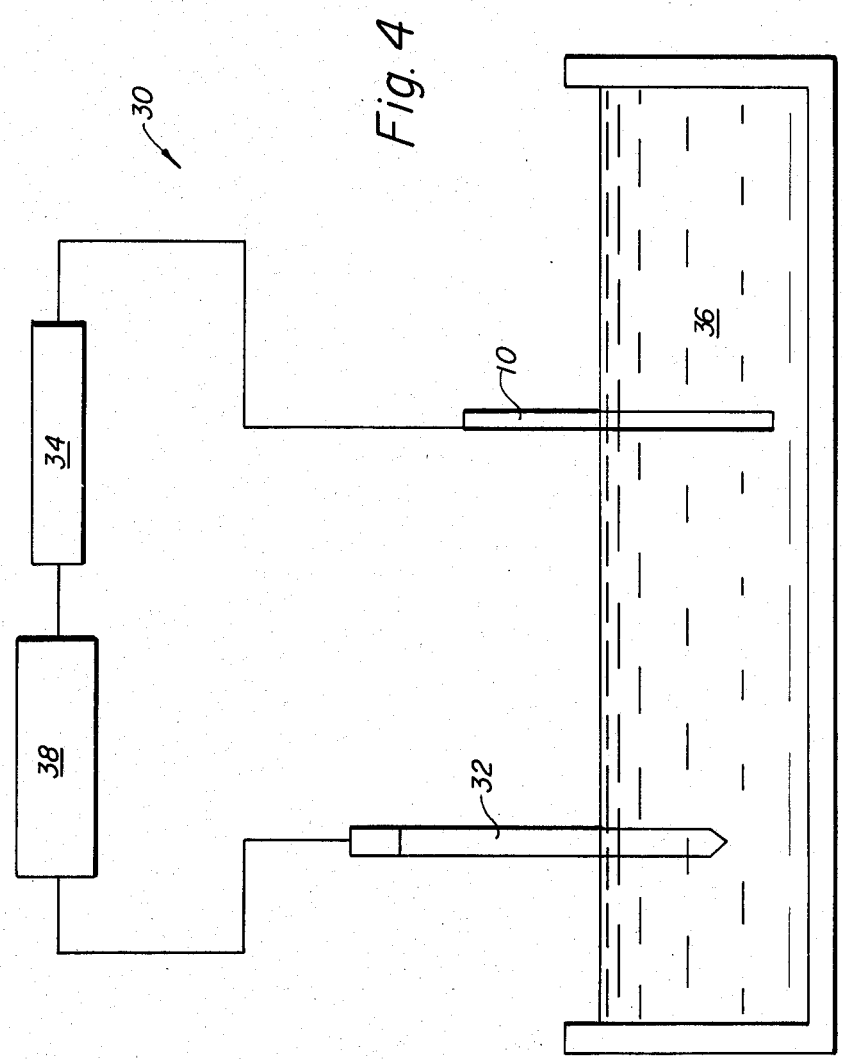

STABILIZED, LIPID MEMBRANE-BASED DEVICE AND METHOD OF ANALYSIS

TECHNICAL FIELD

The present invention relates to a lipid membrane-based device. More specifically, this invention pertains to a lipid membrane-based device useful as a chemoreceptive transducer in an electrochemical cell, and to the use of this device in an electrochemical cell for the analysis of specific chemical test species in an aqueous electrolytic solution.

BACKGROUND ART

A lipid membrane useful as a chemoreceptive transducer in an electrochemical cell is known, as illustrated by Thompson and Krull, *Analytica Chimica Acta*, 147: 1–21 (1983).

A supported lipid membrane is known, as exemplified by Thompson et al, *Analytica Chimica Acta*, 117: 133–145 (1980), Albrecht et al, *Biochimica et Biophysica Acta*, 687: 165–169 (1982), Kuhn, *Thin Solid Films*, 99: 1–16 (1983), and U.S. Pat. No. 4,490,216 to McConnell. Also Krull et al, Abstract 11-2, 67th Annual CIC Conference (June 1984) disclose the use of Langmuir-Blodgett thin-film deposition technology for providing substrate-stabilized, lipid membrane structures, and mention techniques for such deposition including schemes involving lipid-substrate anchorage.

The McConnell patent is directed to a supported, membrane-based device for measuring changes in the membrane surface charge. McConnell's device includes a solid layer that is conductive or semiconductive, and a lipid barrier that electrically insulates the solid layer from a polar layer (col. 13, lines 5–11). The lipid barrier is composed of a first hydrophobic layer that is non-diffusively bound to the solid layer and that is described as being relatively rigid, and a second hydrophobic layer that is bound to the first hydrophobic layer by hydrophobic interactions and that may respond to changes in its environment. Attached to the distal ends of the second hydrophobic layer are polar hydrophilic heads that define the polar layer. At column 12, formation of the first hydrophobic layer by reacting a silylating reagent with the solid layer is described.

There continues to be a need for an improved stabilized, lipid membrane-based device. In particular, there is a need for an ion-permeable device of this type that is useful as a chemo-receptive transducer in an electrochemical cell for the analysis of specific chemical test species. Thus, the discovery of such an improved lipid membrane-based device would constitute a significant contribution to the art. Furthermore, such a device would make possible an improved process for the analysis of specific chemical test species.

DISCLOSURE OF THE INVENTION

It is accordingly an object of the present invention to provide an improved stabilized, lipid membrane-based device.

It is a further object of the present invention to provide an ion-permeable device of this type that is useful as a chemo-receptive transducer in an electrochemical cell for the analysis of specific chemical test species.

It is an even further object to provide an improved process for the analysis of specific chemical test species.

Additional objects, advantages and novel features of the present invention are set forth in the description that follows, and in part will become apparent to those skilled in the art upon examination of the following description or may be learned by practice of the invention.

To achieve the foregoing objects and in accordance with the purpose of the present invention, as embodied and broadly described herein, there is provided a stabilized, ion permeable, lipid membrane-based device. This device includes a plurality of membrane-forming lipids, and a support for stabilizing the membrane formed by the lipids. The lipid membrane includes a complexing agent for selectively interacting with a specified chemical species so as to increase the membrane ion permeability.

Each of the membrane-forming lipids includes a polar head group, a first long chain through which the membrane-forming lipid is anchored to a binding site on the support, and a second long chain unattached to the support.

The binding sites on the support are spaced appropriately apart from one another to provide a lipid molecular packing density that permits axial rotation of each of the membrane-forming lipids about the anchored long chain, and are yet sufficiently close to one another so that the lipid molecular packing density provides a relatively high ion impermeability to the lipid membrane when unperturbed.

Also provided by the present invention is a process for determining the concentration of a selected chemical species in an aqueous electrolytic solution. This process includes forming an electrochemical cell from the aqueous electrolytic solution and the stabilized, ion permeable, lipid membrane-based device of the present invention. There is then applied across the lipid membrane an electrical potential difference that serves to drive ions through, or into and out of, the membrane, whereby the chemical species interacts with the complexing agent incorporated in the membrane, to produce an analytical signal based upon an increased ion permeability of the membrane. The analytical signal is measured, and the concentration of the chemical species is determined from the measured signal.

BRIEF DESCRIPTION OF THE DRAWING

Reference is now made to the accompanying drawing which forms a part of the specification of the present invention.

FIG. 3 is a cross-sectional view along the line 3—3 in FIG. 1; and

FIG. 4 is a diagrammatic view of an electrochemical cell that includes the device of FIG. 1, and that is useful for the analysis of a chemical test species.

BEST MODE FOR CARRYING OUT THE INVENTION

Figure 1:
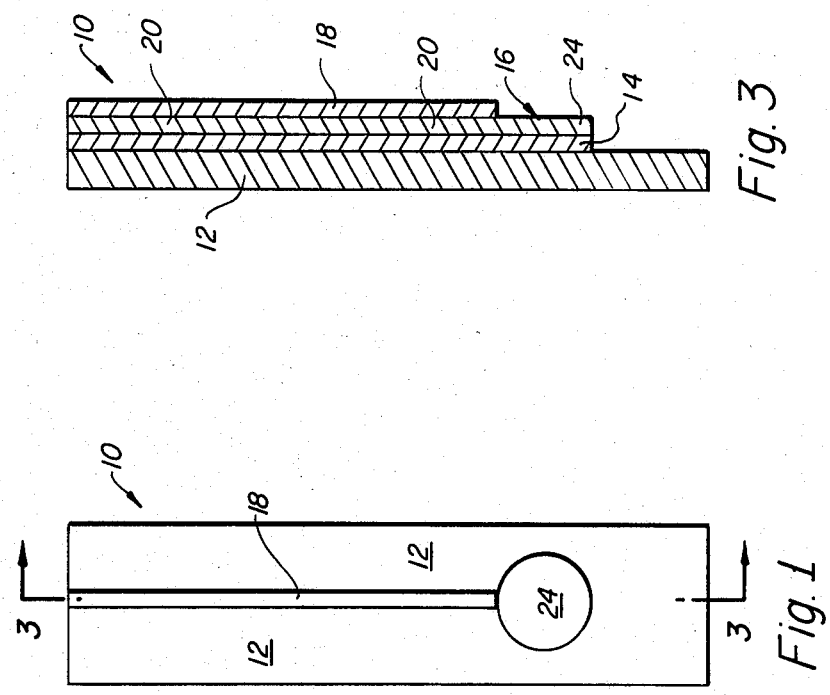
FIG. 1 is a top view of a preferred embodiment of a stabilized, ion permeable, lipid membrane-based device in accordance with the present invention.

As explained earlier, the present invention is directed to a novel ion-permeable, lipid membrane-based device. The membrane of this device is stabilized and has an appropriate molecular packing density. Additionally, this invention is directed to the use of this device as a chemo-receptive transducer in an electrochemical cell for the quantitative or qualitative analysis of specific chemical test species (stimulants) in an aqueous electrolytic solution.

The stabilized, lipid membrane-based device of the present invention includes a perturbable lipid membrane and a membrane-stabilizing support. The lipid membrane is modified by the incorporation of a complexing agent selective for a stimulant. Interaction between the complexing agent and the stimulant produces an increased ion permeability of the lipid membrane, which results in the production of an analytical signal.

Complexing agents, and appropriate densities of complexing agents in lipid membranes are conventional in this art. A complexing agent useful in the device of this invention may be a receptor selective for an organic compound. The receptor, which could, for example, be chemically bound in the lipid membrane, may be a product of nature or a synthetic organic compound. Exemplary receptor-organic compound pairs, all of which are well known, are as follows: antibody-antigen, hormone receptor-hormone, enzyme-substrate, enzyme inhibitor-enzyme, and lectin-polysaccharide. An advantageous glycoreceptor is concanavalin A, which is useful for dextran analysis.

Alternatively, the complexing agent may be selective for an inorganic ion. A useful complexing agent of this type includes a polypeptide such as an antibiotic polypeptide. Illustrative antibiotic polypeptides are well known in this art, and include gramicidin A, valinomycin and nonactin.

The membrane-forming lipids may be natural or synthetic. Suitable lipids include, but are not limited to, phospholipids such as phosphatidic acid, phosphatidyl glycerol, phosphatidyl choline, phosphatidyl ethanolamine, phosphatidyl serine and phosphatidyl inositol; and sphingolipids such as sphingomyelins. Phosphatidyl serine may be advantageously selected for use if biocompatibility is a consideration. These exemplary lipids include a phosphate moiety as a polar head group.

Lipids forming the membrane of this device include two long chains. Any long chain useful in forming a natural or synthetic bilayer or monolayer membrane, is suitable. For purposes of this invention, by the term "long chain" is meant that the chain is at least six carbon atoms in length and not more than about thirty carbon atoms in length. Preferably, a long chain in accordance with this invention is at least six to about twenty carbon atoms in length, with illustrative long chains being acyl chains such as caproyl, lauroyl, myristoyl, palmitoyl and stearoyl. The membrane could be formed by a mixture of suitable lipids.

Each membrane-forming lipid is anchored to a binding site on the support through one of the long chains. This anchored chain may contain functional groups for further polymerization or for modification of membrane fluidity/packing.

A second long chain is not attached to the support, and is thus able to move freely. This long chain provides the fluidity needed for the lipid membrane to be perturbable, and should have a length equal to or less than that of the anchored chain. This chain may contain various functional groups.

In one case of a membrane-forming lipid having a glycerol backbone, the anchored, long chain is covalently bonded to the middle carbon (C-2) of the glycerol backbone, and the freely moving, long chain is covalently bonded to the terminal carbon (C-3) that is unoccupied by the polar head group. In another case, the positions of the anchored and freely moving chains on the backbone are reversed. However, an anchored chain typically will be covalently bonded to an atom located on a backbone moiety between the atom to which a freely moving, long chain is covalently bonded and the atom to which a polar head group is covalently bonded.

The lipid membrane-stabilizing support may be an electrically conductive, solid substrate, or a hydrated polymeric gel such as polyacrylamide. In the case of the electrically conductive, solid substrate, the membrane-forming lipids are anchored to the support surface through binding sites typically formed by chemical modification of the surface.

Illustrative electrically conductive, solid substrates include, but are not limited to, a conductive metal such as silver, platinum and gold, or electrolytic glassy carbon. Electrolytic glassy carbon is prepared by cutting crystalline carbon material along a crystal plane, polishing the cut carbon material, and treating the polished material so that it will function as an electrode in an aqueous solution. Each of these exemplary electrically conductive, solid substrates is amenable to surface modification that provides reactive binding sites.

The anchored, long chain may be bound to the membrane-stabilizing support by covalent bonding, or may be bound by physical bonding such as electrostatic complexation or chemisorption, that would require a very high energy for removal or desorption. In comparison, Langmuir-Blodgett thin-film deposition would produce an unstable bonding due to the presence of only weak van der Waals forces.

When anchorage to the support is by covalent bonding, the anchored chain may include a connecting moiety such as a silicon atom that links the chain to an attachment atom of the reactive binding site. When the connecting moiety is a silicon atom, a precursor lipid compound for reacting with the binding site, would be a silylated lipid preferably having one halide group covalently bound to the silicon atom.

The precursor lipid compound is advantageously synthesized from a head group/backbone moiety. For example, using glycerophosphorylcholine as the starting material, a long chain may be attached to the C-3 carbon on the glycerol backbone. Afterwards, a long chain having a reactive terminus such as a hydroxyl group, may be covalently bonded to the C-2 carbon. Alternatively, the C-3 carbon may be blocked with a protective moiety such as an imidazole; and after attaching a long chain having a reactive terminus to the C-2 carbon, the protective moiety could be replaced with a long chain. The protective moiety could be replaced after anchorage of the precursor lipid compound.

A terminal hydroxyl group is highly suitable for reaction with a silylating agent, and may be beneficially reacted with an approximately equimolar amount of the silylating agent under anhydrous conditions. An advantageous silylating agent is a dialkylmonohalosilane, preferably containing methyl substituents, which forms a dimethylsilyl lipid derivative. The halide group is typically chloride or bromide. An exemplary silylating agent is chlorodimethylsilane. The dimethylsilyl lipid derivative may be reacted with 3-bromopropene to form a precursor lipid compound characterized by a bromodimethylsilyl moiety.

Advantageously, the precursor lipid compound includes a backbone moiety with only a single long chain, and the second long chain is attached after anchorage to the support. However, the precursor lipid compound could include more than one long chain.

Surface modification of the electrically conductive, solid support to provide reactive binding sites can be accomplished through conventional oxidation or nitridation. Oxidation yields hydroxyl binding sites, and nitridation gives nitrogen-containing binding sites. Other possibilities for the reactive binding sites include —SH moities. For example, a platinum substrate may be oxidized with a plasma torch in presence of oxygen, or with aqua regia followed by hydrogen peroxide; a silver substrate may be oxidized with an aqueous solution of about 5% sodium hydroxide; and a glassy carbon surface may be thermally baked at a very elevated temperature in the presence of oxygen.

In forming a covalent bond between the precursor lipid compound and, for example, a hydroxyl binding site on the support, an excess of the lipid compound should be used, suitably about a 2:1 excess, so as to assure occupancy of all binding sites. Reaction of a silicon atom-containing, precursor lipid compound with a hydroxyl binding site forms an —O—Si— covalent linkage between the support and the membrane-forming lipid.

It is essential that the binding sites be spaced sufficiently far apart from one another to provide a lipid molecular packing density that permits axial rotation of each membrane-forming lipid about the anchored, long chain. This degree of spacing provides a lipid membrane that is perturbable by the interaction of the complexing agent with the stimulant.

On the other hand, it is essential that the binding sites on the support surface be sufficiently close to one another to furnish a lipid molecular packing density that provides the lipid membrane with a relatively high ion impermeability when unperturbed. By the term "relatively high ion impermeability" is meant an ion permeability ranging from about $10^{-9}$ to $10^{-13}$ amps/cm$^2$ in 0.1 molar KCl solution for an applied potential of 50 mV across the membrane.

Accordingly, when modification of a support surface is carried out, progress is monitored using a technique such as electron spectroscopy for chemical analysis, so that a suitable binding site density is obtained. A wide range of binding site densities is useful in this invention. However, the binding site density suitable for a particular embodiment of the invention, depends upon factors including the membrane-forming lipid used. More precisely, the average molecular area occupied by the lipid determines whether the degree of spacing between binding sites is sufficient for axial mobility, and for the unperturbed membrane whether the degree of spacing provides relatively high ion impermeability.

For instance, in the case of phosphatidyl choline having one double bond in each of two acyl chains of about 15 to 20 carbons length, the average molecular area is approximately 0.6–0.7 nm$^2$ at a surface pressure of about 32 mNm$^{-1}$. By way of comparison, an identical phosphatidyl choline differing only in having two double bonds per long chain, has an average molecular area ranging from about 0.45–0.55 nm$^2$. For each double bond per chain, the calibration factor is typically about 0.5–1 nm$^2$.

From the above description, it can be understood that a suitable binding site density for a membrane-forming lipid having an average molecular area of about 0.5 nm$^2$, will be about 0.5 nm$^2$.

Preferably, the degree of ion impermeability and the extent of axial mobility are such as to maximize the increase in ion permeability that occurs upon interaction of the complexing agent and the stimulant. Maximization is observed as an optimized signal to noise ratio.

The lipid membrane of the device of the present invention should typically have an ion energy barrier of about 500–2000 meV, preferably about 800–1200 meV. This energy barrier is principally a function of the average molecular area of the selected lipid, and of the dipolar potential, which generally should be in the range of about 400 to 800 mV. Final adjustment of dipolar potential, energy barrier and average molecular area may be achieved by incorporation of unbound lipid molecules into any spaces that may remain between lipids anchored to the support.

The complexing agent is typically incorporated into the lipid membrane after the membrane-forming lipid has been anchored to the support.

The stabilized, ion-permeable, lipid membrane-based device of the present invention is useful in an electrochemical cell for determining the concentration of a stimulant in an aqueous electrolyte solution. When a hydrated polymeric gel is used as the support, the cell may be used to measure ion current. On the other hand, if the electrically conductive, solid substrate is used as the support, the cell may be used to measure change in internal capacitance of the lipid membrane.

A liquid electrochemical cell for analysis of a stimulant will include a stabilized, lipid membrane-based device in accordance with the present invention, a reference electrode, a bridge measurement device such as a capacitance bridge, a power supply and an electrolyte. Such a cell may be used for analysis of a stimulant as follows: Several known concentrations of the stimulant are introduced into the cell, and a calibration curve is prepared by measuring the capacitance change for these known concentrations. Then an unknown concentration of the stimulant is introduced into the cell, the capacitance change is measured, and the concentration is determined by comparison of this capacitance change with the calibration curve.

In the Examples that follow and throughout this description and the claims set forth below, all percentages are by weight/weight, and all procedures are carried out at ambient temperature and pressure, unless otherwise specified.

EXAMPLE 1

Glycerophosphorylcholine is reacted with an approximately equimolar amount of the acid chloride of caproic acid to prepare a glycerophosphorylcholine derivative having a six carbon-containing, acyl chain covalently bound to the C-3 carbon on the glycerol backbone.

Azelaic acid monomethyl ester is refluxed for 1½ hours with thionyl chloride; and the acid chloride product is reacted with sodium borohydride in dioxane for one hour to reduce the acyl chloride group to a hydroxymethylene moiety. A terminal carboxyl group is then formed at the other end of the compound by refluxing with 10% sodium hydroxide for 1½ hours to cleave the methyl ester group.

Two moles of the newly formed carboxylic acid are reacted with one mole of dicyclohexylcarbodiimide in methylene chloride for one hour, to provide an anhydride intermediate. The anhydride intermediate is stirred for thirty hours at 25° C. in chloroform and 4-dimethylaminopyridine with an approximately equimolar amount of the glycerophosphorylcholine derivative, to covalently attach to the C-2 carbon thereof, a nine carbon-containing, acyl chain having a reactive, terminal hydroxyl group.

The resulting glycerophosphorylcholine derivative is stirred under anhydrous conditions for 8 hours with an approximately equimolar amount of chlorodimethylsilane to produce a silylated lipid compound having the six carbon-containing, acyl chain attached to the C-3 carbon, and a dimethylsilyl moiety covalently bound to the end of the C-2, long chain. Stirring the silylated lipid compound with 3-bromo-propene in chloroform for 1½ hours yields a precursor lipid compound characterized by a dimethylbromosilyl moiety covalently bound to the end of the nine carbon-containing, C-2 chain.

An electrolytic, glassy carbon surface is thermally baked at 800° C. in the presence of oxygen. Using electron spectroscopy to monitor the progress of the oxidation, the oxidation is controlled to yield a hydroxyl group density in which the hydroxyl groups are spaced approximately 0.4 nm$^2$ apart. After the precursor lipid compound has been anchored to the support, this density will permit axial rotation of the lipid about the anchored, C-2 chain, and yet will provide a lipid molecular packing density that provides relatively high ion impermeability to the membrane.

Under anhydrous conditions, the precursor lipid compound is reacted with the hydroxyl binding sites on the oxidized glassy carbon support, in a twofold excess relative to the number of binding sites on the support. Afterwards, a 50 Å×50 Å cross-sectional area density of concanavalin A not exceeding more than 50% of the surface of the lipid membrane, is adsorbed by hydrophobic effects into the membrane, to produce a stabilized, lipid membrane-based device in accordance with the present invention.

EXAMPLE 2

Figure 2:
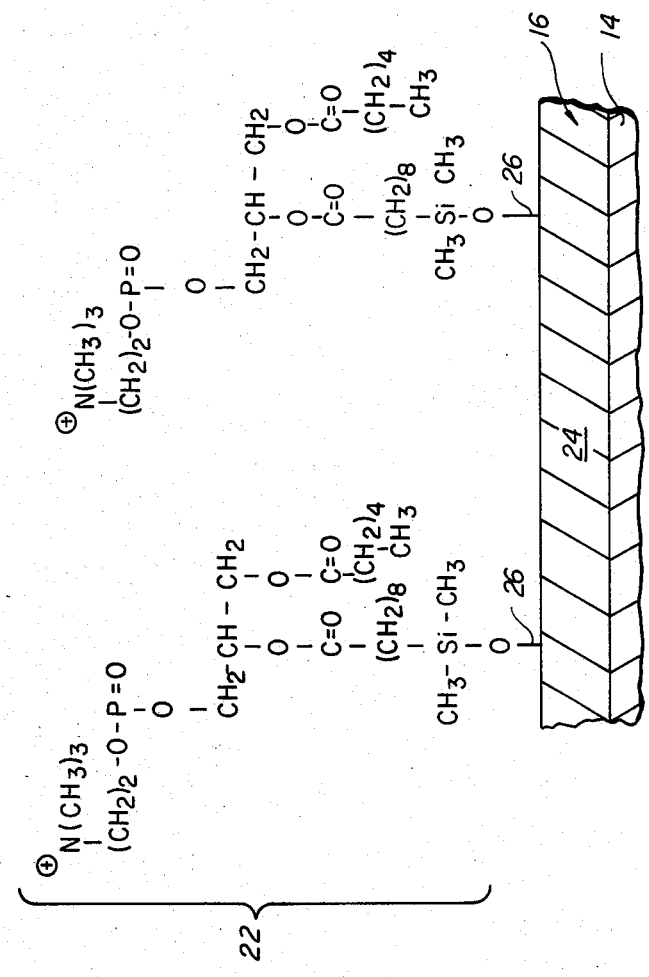
FIG. 2 is a schematic, cross-sectional view of a part of conductive layer 16 of disc-shaped portion 24 of the device of FIG. 1, illustrating the structure of the lipid membrane.

Referring to FIGS. 1-3, a stabilized, lipid membrane-based device 10 in accordance with the present invention, is produced as follows.

A template that will yield device 10, which has the pattern shown in FIG. 1, is placed over a clean glass wafer measuring 1×4×0.1 cm, and the selectively covered, glass wafer is placed in a vacuum chamber. The exposed glass surface is coated by vapor deposition with a Ti/W layer of 20 nm thickness to improve silver layer adhesion, and a silver layer of 100 nm thickness is deposited onto the Ti/W layer.

The template is removed, and a lead portion of the silver layer is protectively coated with a layer of a hydrophobic, non-conductive epoxy resin prepared by mixing 100 parts of a liquid diglycidyl ether of bisphenol A available as Epon ® 825 from Shell Chemical Company, 37 parts of a polyoxypropylenediamine available as Jeffamine ® D-230 from Texaco Chemical Company, and 5% of a silica-based, hydrophobic thixatrope available as Cab-O-Sil ® TS-720 from Cabot Corp. The non-conductive epoxy resin coating is cured by standing at ambient room conditions for a period of 12 hours, and then baking at 60° C. for 3 days.

A disc-shaped portion of the silver layer is oxidized with an aqueous 5% sodium hydroxide solution to form hydroxyl groups on the surface thereof. The oxidation is controlled to yield a hydroxyl group density in which the hydroxyl groups are spaced approximately 0.4 nm$^2$ apart.

Under anhydrous conditions, the precursor lipid compound of Example 1 is reacted with the hydroxyl binding sites on the disc-shaped portion of the silver layer in a twofold excess relative to the number of binding sites on the oxidized support. Afterwards, a 50 Å×50 Å cross-sectional area density of concanavalin A not exceeding more than 50% of the surface of the lipid membrane, is adsorbed by hydrophobic effects into the membrane, to produce stabilized, lipid membrane-based device 10.

Referring to FIGS. 1-3, device 10 includes a support 12 (glass wafer), a layer 14 (Ti/W) selectively coated thereon for improved adhesion of a conductive layer 16 to support 12, a conductive layer 16 (silver) deposited over layer 14, a non-conductive protective layer 18 deposited over a lead portion 20 of layer 16, and a lipid membrane 22 covalently bonded to a disc-shaped portion 24 of layer 16. As schematically illustrated in FIG. 2, membrane-forming lipid molecules are spaced apart a distance "d", which is approximately 0.4 nm$^2$.

The chemical and physical structure shown in FIG. 2 for device 10 is merely illustrative of the present invention. For example, as explained earlier, strong physical bonding could be used to anchor the membrane-forming lipids, and reactive binding sites other than hydroxyl groups, could be used for covalent bonding.

EXAMPLE 3

A liquid electrochemical cell 30, as diagrammatically shown in FIG. 4, is prepared using lipid membrane-based device 10 of Example 2, a reference electrode 32 (a platinum microelectrode), a bridge measurement device 34 (a capacitance bridge), and an electrolyte 36 (0.1M KCL at pH 7). An AC potential of +/−25 mV is applied from a power supply 38 at a frequency of 100 hertz. Cell 30 is employed using several known concentrations of dextran to prepare a calibration curve. Then an aqueous sample containing an unknown concentration of dextran is introduced into the electrochemical cell, the capacitance change is measured, and the concentration of dextran is determined to be $10^{-6}$M by comparison of the capacitance change with the calibration curve.

The above examples are illustrative of the present invention. It is to be understood that these examples are not in any way to be interpreted as limiting the scope of the invention. Rather, it is intended that the scope of the invention be defined by the claims set forth below. It is contemplated that the invention as hereinafter claimed, will be subject to various modifications, which modifications are within the scope thereof.

Industrial Applicability

The stabilized, lipid membrane-based device of this invention is useful as a chemo-receptive transducer in an electrochemical cell, for the analysis of specific chemical test species in an aqueous electrolytic solution.

We claim:

1. A stabilized, lipid membrane-based device comprising a perturbable lipid membrane and a membrane-stabilizing support, said lipid membrane including a complexing agent for selectively interacting with a specified chemical species to perturb said lipid membrane;

wherein each membrane-forming lipid includes a polar head group, a first long chain through which the lipid is anchored to a binding site on said support, and a fluidity-providing, second long chain, which is unattached to said support; and wherein the binding sites on said support are spaced appropriately apart from one another to provide a lipid molecular packing density that permits axial rotation of each membrane-forming lipid about its anchored, long chain, and are yet sufficiently close to one another so that said lipid molecular packing density provides a relatively high ion impermeability to said lipid membrane when unperturbed;

said lipid membrane having an increased ion permeability when perturbed.

2. The device of claim 1, wherein said support is an electrically conductive, solid substrate.

3. The device of claim 2, wherein said electrically conductive, solid substrate is electrolytic glassy carbon.

4. The device of claim 2, wherein said electrically conductive, solid substrate is an electroconductive metal.

5. The device of claim 4, wherein said electroconductive metal is silver.

6. The device of claim 1, wherein said first long chain is anchored by covalent bonding.

7. The device of claim 1, wherein said membrane-forming lipid is a phospholipid.

8. The device of claim 7, wherein said phospholipid is phosphatidyl choline.

9. The device of claim 7, wherein said phospholipid is phosphatidyl serine.

10. The device of claim 1, wherein said first and second long chains are acyl chains.

11. The device of claim 1, wherein said complexing agent is a natural product.

12. A process for determining the concentration of a selected chemical species in an aqueous electrolytic solution, said process comprising
   (a) form electrochemical cell from the device of claim 1 and said aqueous electrolytic solution;
   (b) applying across said lipid membrane an electrical potential difference that serves to drive ions through, or into and out of, said membrane, whereby said chemical species interacts with said complexing agent incorporated in said lipid membrane, to produce an analytical signal based upon an increase in membrane ion permeability;
   (c) measuring said analytical signal; and
   (d) determining said chemical species concentration from the measured analytical signal.

13. The process of claim 12, wherein capacitance is measured.

14. The process of claim 12, wherein said chemical species is an organic compound.

15. The process of claim 12, wherein said chemical species is an inorganic ion.

* * * * *